US012577527B2

(12) United States Patent
Luo et al.

(10) Patent No.: US 12,577,527 B2
(45) Date of Patent: Mar. 17, 2026

(54) STRAIN FOR DEGRADING DEOXYNIVALENOL AND USE THEREOF

(71) Applicant: INSTITUTE OF ANIMAL SCIENCE OF CHINESE ACADEMY OF AGRICULTURAL SCIENCES, Beijing (CN)

(72) Inventors: Huiying Luo, Beijing (CN); Honghai Zhang, Beijing (CN); Bin Yao, Beijing (CN); Huoqing Huang, Beijing (CN); Yaru Wang, Beijing (CN); Yingguo Bai, Beijing (CN); Xiaoyun Su, Beijing (CN); Yuan Wang, Beijing (CN); Tao Tu, Beijing (CN); Jie Zhang, Beijing (CN); Huimin Yu, Beijing (CN); Xing Qin, Beijing (CN); Xiaolu Wang, Beijing (CN)

( * ) Notice: Subject to any disclaimer, the term of this patent is extended or adjusted under 35 U.S.C. 154(b) by 280 days.

(21) Appl. No.: 18/254,176

(22) PCT Filed: Nov. 11, 2021

(86) PCT No.: PCT/CN2021/129928
§ 371 (c)(1),
(2) Date: May 24, 2023

(87) PCT Pub. No.: WO2022/111287
PCT Pub. Date: Jun. 2, 2022

(65) Prior Publication Data
US 2024/0093142 A1 Mar. 21, 2024

(30) Foreign Application Priority Data
Nov. 26, 2020 (CN) .......................... 202011347741.9

(51) Int. Cl.
| | |
|---|---|
| C12N 1/20 | (2006.01) |
| A23L 5/20 | (2016.01) |
| B09C 1/10 | (2006.01) |
| C02F 3/34 | (2023.01) |
| C02F 101/34 | (2006.01) |
| C12N 1/205 | (2026.01) |
| C12R 1/01 | (2006.01) |

(52) U.S. Cl.
CPC ................ *C12N 1/205* (2021.05); *A23L 5/28* (2016.08); *B09C 1/10* (2013.01); *C02F 3/34* (2013.01); *C02F 2101/34* (2013.01); *C12R 2001/01* (2021.05)

(58) Field of Classification Search
CPC ... C12N 1/205; A23L 5/28; B09C 1/10; C02F 3/34; C02F 2101/34; C12R 1/01
See application file for complete search history.

(56) References Cited

PUBLICATIONS

Sato I, Ito M, Ishizaka M, et al. Thirteen novel deoxynivalenol-degrading bacteria are classified within two genera with distinct degradation mechanisms. FEMS Microbiol Lett. 2012;327(2):110-117. doi:10.1111/j.1574-6968.2011.02461.x.
Ikunaga Y, Sato I, Grond S, et al. *Nocardioides* sp. strain WSN05-2, isolated from a wheat field, degrades deoxynivalenol, producing the novel intermediate 3-epi-deoxynivalenol. Appl Microbiol Biotechnol. 2011;89(2):419-427. doi:10.1007/s00253-010-2857-z.
International Search Report; Feb. 17, 2022.

*Primary Examiner* — Robert A Zeman
(74) *Attorney, Agent, or Firm* — Patshegen IP; Moshe Pinchas

(57) ABSTRACT
The present invention relates to the fields of microorganisms, feed, food and ecological restoration, in particular to a strain for degrading deoxynivalenol (DON) and the use thereof. The strain has the deposit number CCTCC No. M 2020565. The strain can grow by means of taking the toxic compound DON as a sole carbon source, and convert the DON into chemical components for itself. The reaction process is irreversible, the reaction conditions are moderate, and secondary pollution cannot be caused. The strain provided in the present invention can be used for preparing a biological detoxification preparation for DON. The strain provided in the present invention can be used for degrading DON in feed and food raw materials, primary processing products, deep processing products and related processing byproducts. The strain provided in the present invention can be applied to various ecosystems such as soil or bodies of water polluted by DON to achieve the purposes of DON degradation and ecological restoration.

4 Claims, 2 Drawing Sheets

STRAIN FOR DEGRADING DEOXYNIVALENOL AND USE THEREOF

FIELD OF THE INVENTION

The present invention relates to the field of microorganisms, in particular to a strain for degrading deoxynivalenol and application thereof.

BACKGROUND OF THE INVENTION

Deoxynivalenol (DON) can cause vomiting in humans and animals, thus is also called vomitoxin. It is a common food borne mycotoxins and widely exists in food raw materials such as wheat, barley, oats and corn. The physicochemical properties of DON are extremely stable, and it is difficult to remove it using general cooking and processing techniques. During high-temperature baking, it can be converted into other compounds with unknown toxicity, such as nor-DON, DON lactones, etc. In addition, DON can exist in plants in a "hidden" form, such as 3-β-D-glucose-DON. This "hidden" form of derivative is considered a product of plant self-defense. Unfortunately, concealed DON can still be changed back to DON through the action of gut microbiota, further increasing the risk of exposure to humans and animals.

The biodegradation technology of DON has attracted widespread attention in recent years due to its high efficiency, green color, mild reaction conditions, and ease of large-scale application. However, the biological resources available for research and application are very scarce. The acquisition of pure culture of DON degrading strains and the revelation of their degradation mechanisms will provide important insights for the development of DON degrading products Devosia is a widely studied type of DON degrading strain. Multiple species and subspecies in the genus DeVos have been confirmed to be able to degrade DON into 3-keto-DON and 3-epi-DON. In 2018, Zhou Ting's team in Canada confirmed that two enzymes, DepA and DepB, were responsible for these two degradation processes. Subsequently, multiple teams have also confirmed that independently isolated DeVostonia can transform DON, but not all DeVostonia can achieve the above two steps of transformation.

*Nocardioides* has been found to be able to degrade DON almost simultaneously with Devotella. In the publications, only Tsushima Group in Japan has reported that *Nocardioides* can fully convert and utilize DON as a carbon source. During the degradation process of DON by *Nocardioides,* 3-epi-DON is produced, which is further transformed. However, the complete degradation mechanism has not been thoroughly studied, and one of the main reasons is that *Nocardioides* strains with DON degradation function are very rare, making it difficult to enrich and isolate pure culture.

SUMMARY OF THE INVENTION

In order to solve the above technical problems, one objective of the present invention is to provide a *Nocardioides* strain for degrading deoxynivalenol.

The another objective of the present invention is to provide a biological detoxification agent comprising said *Nocardioides* strain.

The still another objective of the present invention is provide a method for preparing said biological detoxification agent.

The present invention provides a new *Nocardioides* strain ZHH-013 which was deposited on Sep. 30, 2020 at China Center for Type Culture Collection with the deposit number of CCTCC NO: M 2020565. The strain of the present invention has the similar function to that of *Nocardioides* WSN05-2, and less than 97% homology of 16s rDNA, and is identified as a new species of *Nocardioides* genus by comparing the morphological, molecular biological, physiological and biochemical characteristics with those of the related mode strains.

The *Nocardioides* strain ZHH-013 of the present invention was grown in the fermentation medium containing 10 g tryptone, 5 g yeast extract powder, 10 g sodium chloride, and 1.5% agar, with the pH adjusted to 7.0-7.2, being added to the distilled water to 1 L, and sterilizing at 121° C. for 20 minutes.

The biological detoxification agent according to the present invention comprises the *Nocardioides* strain ZHH-013 with the deposition number of CCTCC NO: M 2020565 or cell inclusions thereof such as the intracellular protein, as active component. The said biological detoxification agent may be in a liquid dosage form or a solid dosage form which is prepared by a preparation method disclosed in the prior art.

Also, The invention provides a preparation method of the biological detoxification agent, which comprises the following steps of activating the *Nocardioides* strain ZHH-013 of present invention, performing its expand culture in multistage, and collecting the fermentation broth in a stable phase, to prepare the liquid biological detoxification agent.

According to the preparation method of the biological detoxification agent of the present invention, wherein the said fermentation broth is concentrated into the high concentration bacterial suspension by natural sedimentation, centrifugation, filtration and other methods that do not affect the activity of the strain. More preferably, the said bacterial suspension can also be added to a nutrient solution or a mixed solution of a nutrient solution and a protective agent to prepare a liquid biological detoxifier. Further, the said liquid biological detoxification agent can be prepared into a solid biological detoxification agent by using methods available in the art, such as adding adsorbents and protective agents and the like.

The preparation method of the biological detoxification agent according to the present invention further comprises the steps of breaking the obtained bacterial suspension or thallus cells by the methods disclosed in the prior art such as homogenization, ultrasound and the like, removing the impurities such as thallus cell debris and the like, and obtaining the protein solution with higher concentration as the biological detoxification agent in liquid form by concentration. The said the biological detoxification agent in liquid form can be prepared into the solid form by the method disclosed in the prior art, such as adding an adsorbent and a protective agent and the like.

The biological detoxification agent can be packaged by conventional packaging techniques in the art and stored according to specific environmental conditions.

The advantages of the present invention are:

(1) The invention isolates a *Nocardioides* strain with DON degradation function from soil in China, wherein the DON degradation function of the strain is similar to that of a reported the Nocardia-like strain separated in Japan, and their 16s rDNA homology is less than 97%.

(2) The strain provided by the invention is by the classification methods of morphology, physiology and biochemistry and 16S rDNA sequence analysis, and is determined to be a new species of *Nocardioides* by comparing the morphological, physiological and biochemical characteristics with those of the relative model strain.

(3) The strain provided by the present invention can grow with the toxic compound DON as the sole carbon source by converting DON into its own chemical composition, which is an irreversible and mild reaction without secondary pollution.

(4) The strain provided by the invention can be used for preparing various biological detoxification agents of DON.

(5) The strain provided by the present invention and various DON biological detoxification preparations prepared by it can be used for degrading DON in feed and food raw materials, primary processing products, deep processing products and related processing byproducts.

(6) The strains provided by the present invention and various DON detoxification preparations prepared therefrom can be applied to various ecosystems such as soil or water contaminated by DON, to degrade DON and repair ecological bodies.

BRIEF DESCRIPTIONS OF THE DRAWINGS

Figure 1:
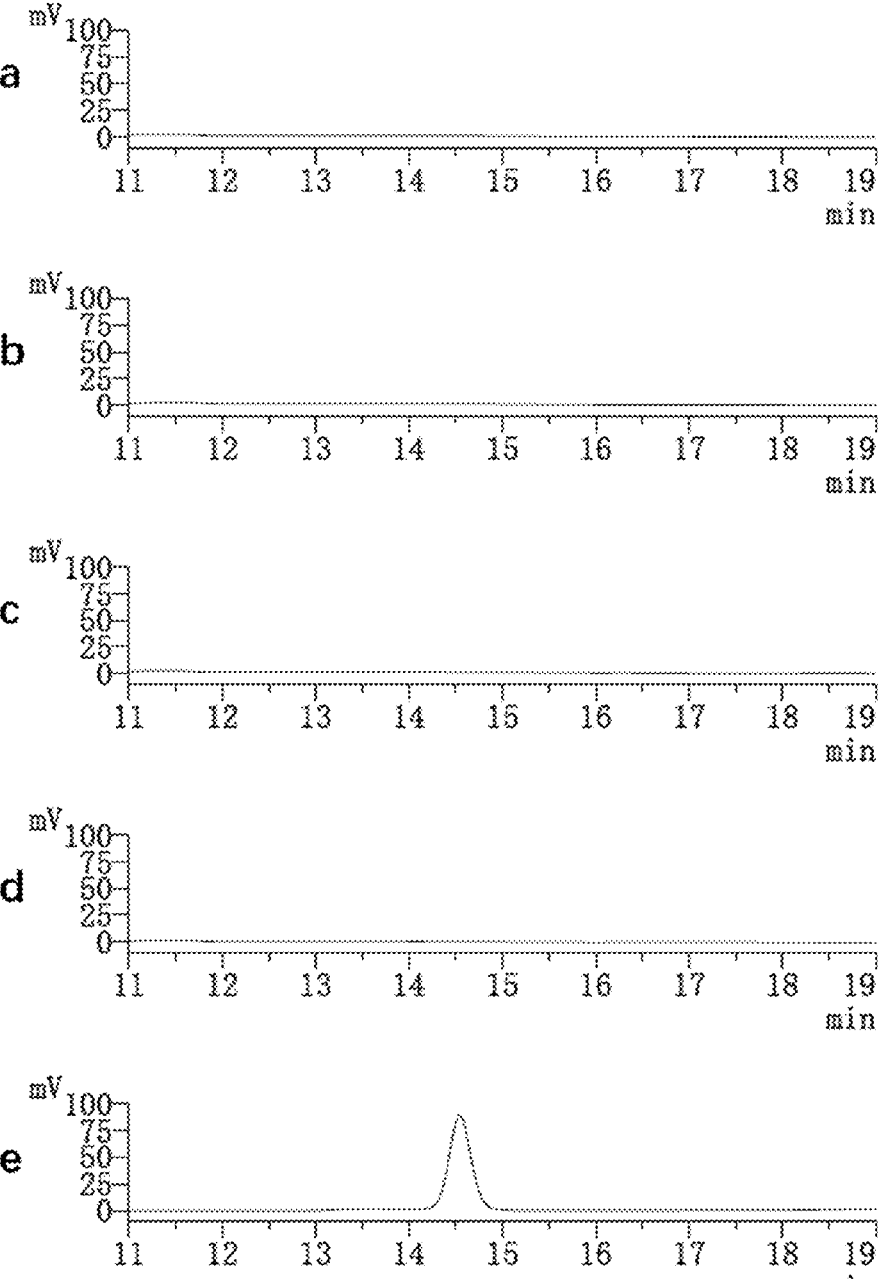
FIG. 1 is a chromatogram ($RT_{DON}=14.9$) of DON degradation by *Nocardioides* strain ZHH-013 of the present invention and its endolysate.

*Nocardioides* sp. ZHH-013 with the deposit number CCTCC No: M 2020565 was deposited in the China Typical Culture Collection Center in Wuhan University, Wuhan, China on Sep. 30, 2020.

EMBODIMENT

Example 1 Isolation and Identification of Deoxynivalenol-Degrading Strain

Soil samples were collected from Zhangjiakou City, Hebei Province, China and enriched by shaking flask method, wherein the samples were first prepared into bacterial suspension in sterile water and inoculated into LB liquid medium with the final concentration of DON of 50 μg/mL, with 10% inoculation amount and cultured for 7 days, followed by being transplanted with 10% inoculation amount, remaining the concentration of DON unchanged. After being transplanted 5 times in a row, the content of DON was detected taking the uninoculated DON-LB medium containing the same DON concentration as the negative control. Then, the bacterial suspension in which DON was degraded was coated on LB agar plate with appropriate dilution referring to dilution coating method followed by being cultured at 30° C. for 72 h, and the single colonies with good separation degree and different colony morphology was selected for detoxication test wherein the colonies were inoculated in LB medium with DON concentration of 50 μg/ml and the DON concentration was determined as above. Finally, a strain capable of degrading DON was obtained, and numbered as ZHH-013. Single colonies of the strain ZHH-013 were selected and cultured in LB liquid medium, and harvested at mid-exponential phase to be mixed with 50% glycerol for being stored at −80° C.

The degradation strain of the present invention was identified by morphological, physiological and biochemical methods and 16S rDNA sequence analysis, wherein the round white colonies with a diameter of 1 mm, neat edges, glossy surface, transparent circles around the colonies can be seen in case of being cultured on LB agar medium at 30° C. for 7 days, the round white colonies with neat edges and glossy surfaces can be seen in case of being cultured on TSB agar medium at 30° C. for 7 days, transparent circles appeared around the colonies in case of being cultured on TSB agar medium at 30° C. for 14 days, and gram staining results were positive.

LB culture medium which used in this examples comprises 10 g tryptone, 5 g yeast extract, 10 g sodium chloride, 1.5% agar, dissolved in the distilled water to 1 L, with pH 7.0-7.2, sterilized at 121° C. for 20 minutes.

And, the TSB culture medium which used in this examples was purchased.

All results indicate that the ZHH-013 strain should be classified as *Nocardioides* sp., based on direct laboratory comparisons and retrieval of published descriptions of similar species.

Example 2 Strain is Used for Degrading Deoxynivalenol

1. Detection Method of DON

Preparation of DON solution: Dissolving 5.0 mg of DON standard in 1 mL of sterile water to obtain a final concentration of 5 mg/mL of DON solution which is sterilized with a 1 ml syringe filter, is stored at −20° C. and is valid for 3 months.

Sample preparation: Adding equal volume of pure methanol to 500 μL of sample solution, shaking and mixing well, centrifuging at 12000 rpm at 4° C. for 10 minutes, and separating 500 μL of supernatant for HPLC detection of DON, with Agilent 5 TC-C18 chromatographic column, reverse phase chromatographic column in of 250×4.6 mm, 5 μm, mobile phase of methanol: water in 15:85, equal degree elution, flow rate in 1 mL/min, injection volume of 20 μL, column temperature of 30° C., UV detection wavelength of 220 nm, and retention time of DON of 14.9 minutes.

2. The monoclone of *Nocardioides* sp. ZHH-013 was picked from the plate, inoculated into 3 mL of LB medium, cultured at 30° C. for 7 days, and transferred to 3 mL of LB medium with a final concentration of 50% of DON with 1% of inoculation volume for shaking culture at 30° C. for 3 days, followed by determining the content of DON using the above method in which the experimental group without DON was taken as the negative control. The chromatographic analysis results are shown in FIG. 1, wherein "a" represents the control only inoculated with bacterial solution, "e" represents the control only with DON, and "b" and "c" represent the complete degradation of DON compared to the control after overnight cultivation in two treatment groups.

3. Degradation of DON by Crude Enzyme Solution

The bacterial body is prepared according to the above step 2, and resuspended in PBS buffer of pH 6.9 with the $OD_{600}$ of 1.0, followed by being broken with an ultrasonic crusher, and centrifuging at 12000 rpm and 4° C. for 10 minutes to obtain the supernatant. 10 μL of DON solution and was added to 490 μL of supernatant to a final concentration of 50 μg/mL for overnight cultivation, followed by measuring the content of DON using the above method. The chromatographic analysis results are shown in "d" of FIG. 1, indicating that DON was completely degraded.

4. Degradation of DON in Corn Steep Liquor by Strains

Figure 2:
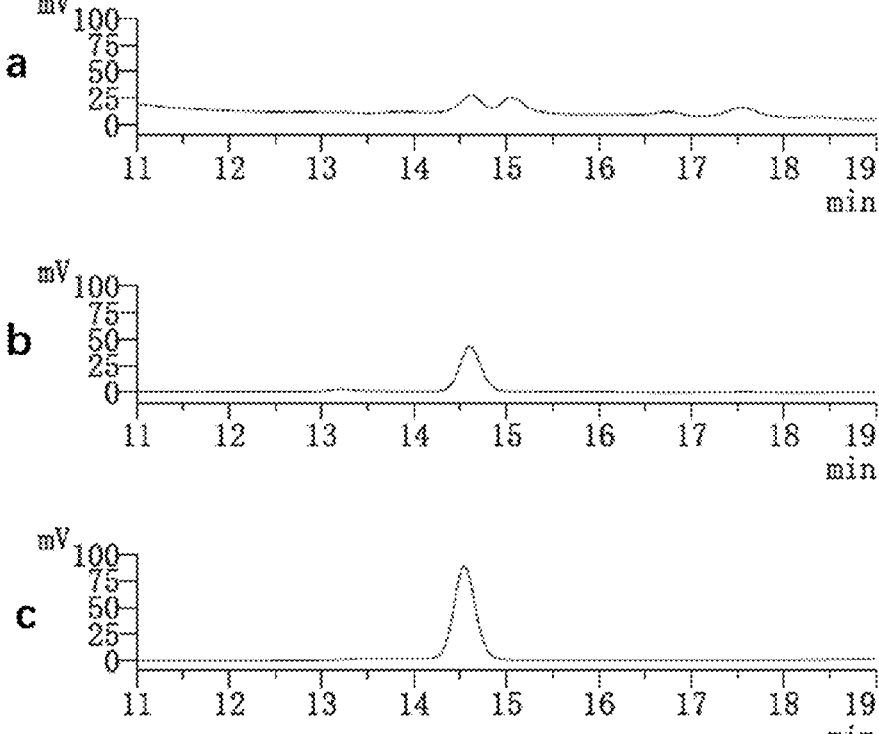
FIG. 2 shows the degradation effect of the *Nocardioides* strain ZHH-013 of the present invention on DON in corn steep liquor.

Monoclone of *Nocardioides* sp. Strain ZHH-013 were selected and inoculated into 3 mL of LB medium for culture of 7 days at 30° C., followed by being transferred to 300 mL of LB medium with 1% of inoculation volume and shaken for culture of 5 days at 30° C. to collect the bacterial bodies which be washed thoroughly with sterile water at least 3 times to completely remove the culture medium, and fully resuspended in PBS buffer of pH 6.9 to adjust the $OD_{600}$ to around 1.0. And, 10% of corn steep liquor aqueous solution was added for overnight cultivation, using the sample without 10% corn syrup aqueous solution as the control, followed by measuring the content of DON according to the above method. The chromatographic analysis results are shown in FIG. 2 wherein "a" is the treatment group with 10% corn slurry aqueous solution, "b" is the treatment group without 10% corn slurry aqueous solution added, and "c" is the control group with neither corn slurry nor degradation strains added. Compared with control group "c", the degradation rate of DON in treatment group "a" after overnight cultivation is greater than 80%, and the DON content in treatment group "b" is also significantly reduced. Therefore, with or without addition of corn syrup aqueous solution, DON can be degraded, and the degradation function of the strain of the present invention is stable, and will not change with the changes in substrate composition.

5. Strain Grows with DON as the Sole Carbon Source

Monoclones of *Nocardioides* sp. Strain ZHH-013 were picked and inoculated onto 1 mL of M9D medium for 7 days of cultivation at 30° C., followed by being transferred once every 7 days according to the transfer method for 3 times. The fermentation broth after each 7 days of cultivation was collected wherein 150 μL of fermentation broth was taken to coat on LB agar plate for cultivation, and the remaining was measured for DON content with the above method. In this example, the formula of said M9D culture medium is M9 culture medium (Difco) with 50 mg of DON, pH of 7.0, dissolving in the distilled water to 1 L, and the strain is transfer to 1 mL of M9D medium with 1% of inoculation volume for cultivating at 30° C. for 7 days.

In this example, transferring 3 times in a row means that the bacterial solution will be diluted 1000 times each time. If DON can not be used as carbon source, it can not be degraded in three consecutive experiments. The rule of colony number on LB agar plate is that the more times of dilution, the less the colony number. And, if DON can be used as a carbon source, the number of colonies will increase after each culture, DON can be degraded in three experiments, and the number of colonies on the LB agar plate for each culture is large and equivalent.

The experimental results showed that the degradation rate of DON in the fermentation broth collected each time was greater than 80%, and the corresponding LB agar plates were covered with lawn of *Nocardioides* sp. ZHH-013, indicating that *Nocardioides* sp. strain ZHH-013 can grow with DON as the sole carbon source.

Obviously, the above embodiments of the present invention are only examples to clearly illustrate the present invention, but not limiting the implementation methods of the present invention. For the person skilled in the art, different forms of modification can be made based on the above illustration. It is impossible to exhaustively list all implementation methods here, so any obvious changes or variations arising from the technical solution of the present invention still fall into the protection scope of the present invention.

The invention claimed is:

1. A method for preparing a biological detoxification agent, including the steps of culturing the *Nocardioides* sp. strain ZHH-013 deposited at the China Center for Type Culture Collecting with the deposit number of CCTCC No. M2020565;

multistage expansion culturing said strain; and collecting fermentation broth and obtaining the said biological detoxicating agent.

2. The method for preparing a biological detoxification agent according to claim 1, wherein the said *Nocardioides* sp. strain ZHH-013 is prepared into a liquid or solid form of a biological detoxification agent.

3. The application of a biological detoxification agent including the *Nocardioides* sp. strain ZHH-013 deposited at the China Center for Type Culture Collecting with the deposit number of CCTCC No. M2020565 to degrade deoxynivalenol in an ecosystem contaminated with deoxynivalenol.

4. A method for degrading deoxynivalenol in feed and food raw materials, primary processed products, further processed products and related processing by-products comprising the administration of the *Nocardioides* sp. strain ZHH-013.

* * * * *